(12) United States Patent
Shindo et al.

(10) Patent No.: US 12,138,005 B2
(45) Date of Patent: Nov. 12, 2024

(54) DRAPE UNIT

(71) Applicant: RIVERFIELD INC., Tokyo (JP)

(72) Inventors: Koki Shindo, Tokyo (JP); Naoya Morita, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 860 days.

(21) Appl. No.: 17/292,247

(22) PCT Filed: Nov. 6, 2020

(86) PCT No.: PCT/JP2020/041562
§ 371 (c)(1),
(2) Date: May 7, 2021

(87) PCT Pub. No.: WO2021/166336
PCT Pub. Date: Aug. 26, 2021

(65) Prior Publication Data
US 2023/0000580 A1    Jan. 5, 2023

(30) Foreign Application Priority Data

Feb. 18, 2020 (JP) .................................. 2020-025698

(51) Int. Cl.
*A61B 46/10* (2016.01)
*A61B 1/00* (2006.01)
(Continued)

(52) U.S. Cl.
CPC .......... *A61B 46/10* (2016.02); *A61B 1/00142* (2013.01); *A61B 34/30* (2016.02);
(Continued)

(58) Field of Classification Search
CPC ..... A61B 46/10; A61B 1/00142; A61B 34/30; A61B 50/00; A61B 50/20; A61B 50/30;
(Continued)

(56) References Cited

U.S. PATENT DOCUMENTS

| 2017/0151028 A1 | 6/2017 | Ogawa et al. |
| 2018/0078325 A1* | 3/2018 | Yanagihara ............ A61B 34/32 |
| 2019/0159853 A1 | 5/2019 | Haraguchi et al. |

FOREIGN PATENT DOCUMENTS

| CN | 109640866 A | 4/2019 |
| EP | 3291756 A1 | 3/2018 |
| (Continued) | | |

OTHER PUBLICATIONS

Communication dated Dec. 16, 2021, issued by the State Intellectual Property Office of the P.R.C. in application No. 202080005572.2.
(Continued)

*Primary Examiner* — Tarla R Patel
(74) *Attorney, Agent, or Firm* — Sughrue Mion, PLLC

(57) ABSTRACT

An aspect of the present invention provides a drape unit that is disposed between a medical robot holding a surgical instrument and the surgical instrument to isolate the surgical instrument and the medical robot from each other. The drape unit transmits power in a forward/backward direction from a power transmission part of the medical robot to a movable part provided in the surgical instrument. The drape unit comprises: a movable intervening part that receives the power from the power transmission part; and a fixed intervening part that is detachably attached to the medical robot. The fixed intervening part has a through-hole through which a part of the movable intervening part is inserted. The fixed intervening part has a housing portion that covers a part of the movable intervening part as viewed in a penetrating direction of the through-hole when the movable intervening part moves to an end portion in the forward/backward direction. It is thereby possible to sufficiently isolate a clean area and an unclean area from each other and improve the operability of surgery.

20 Claims, 12 Drawing Sheets

(51) Int. Cl.
   *A61B 17/00* (2006.01)
   *A61B 34/30* (2016.01)
   *A61B 50/00* (2016.01)
   *A61B 50/20* (2016.01)
   *A61B 50/30* (2016.01)
(52) U.S. Cl.
   CPC .............. *A61B 50/00* (2016.02); *A61B 50/20* (2016.02); *A61B 50/30* (2016.02); *A61B 2017/00367* (2013.01); *A61B 2017/00398* (2013.01)
(58) Field of Classification Search
   CPC  A61B 2017/00367; A61B 2017/00398; A61B 90/40; A61B 34/70
   See application file for complete search history.

(56) References Cited

FOREIGN PATENT DOCUMENTS

| | | |
|---|---|---|
| EP | 3305238 A1 | 4/2018 |
| JP | 6138396 B2 | 5/2017 |
| WO | 2016/178028 A1 | 11/2016 |

OTHER PUBLICATIONS

Extended European Search Report dated Mar. 17, 2022 from the European Patent Office in EP Application No. 20904251.4.
Office Action dated Sep. 9, 2022 issued by the European Patent Office in European Application No. 20 904 251.4.

* cited by examiner

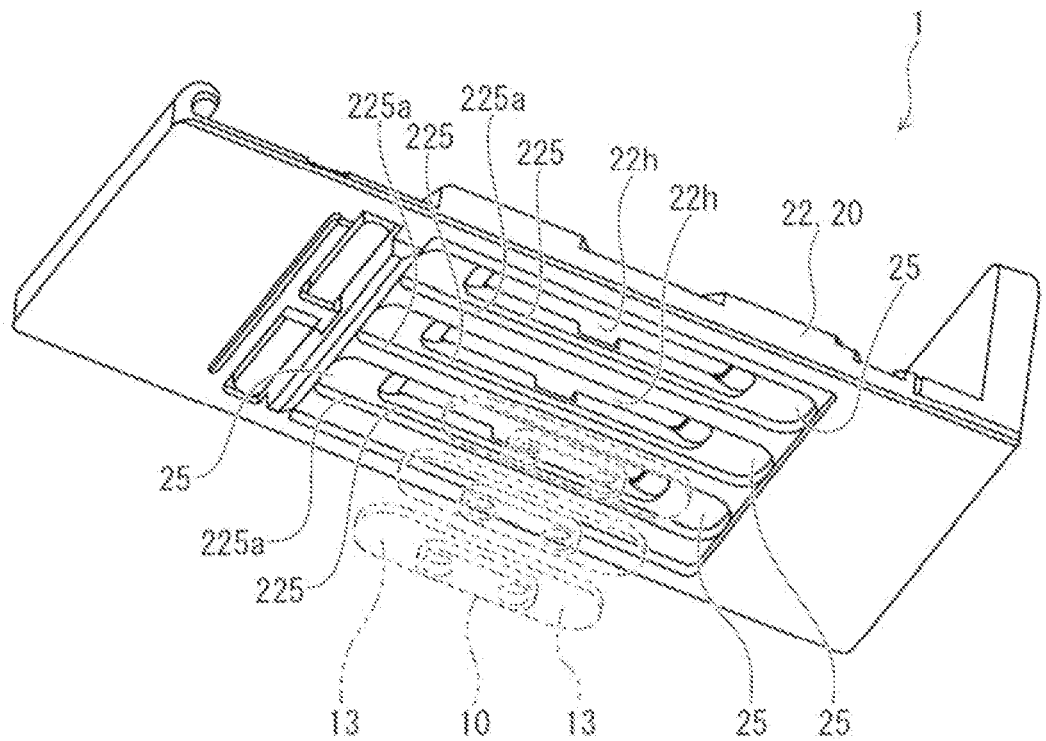
FIG. 10
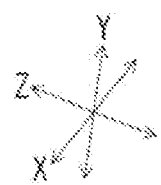

DRAPE UNIT

CROSS REFERENCE TO RELATED APPLICATIONS

This application is a National Stage of International Application No. PCT/JP2020/041562 filed Nov. 6, 2020, claiming priority based on Japanese Patent Application No. 2020-025698 filed Feb. 18, 2020, the entire contents of each of which being herein incorporated by reference in their entireties.

TECHNICAL FIELD

The present invention relates to a drape unit that isolates a medical robot and a surgical instrument.

BACKGROUND ART

Surgery using medical robots is attracting attention as a technique that enhances the possibility of not only reducing the burden on a surgeon but also the burden on a patient as well as the possibility of remote medical care through highly accurate and stable treatment. When using a medical robot, the surgical instrument is sterilized and therefore is a clean area, but the medical robot side is not as sterilized as the surgical instrument side and is therefore an unclear area. For this reason, in surgery using a medical robot, the medical robot side is covered with a drape in order to isolate the clean area and the unclean area from each other.

Patent Document 1 discloses a surgical robotic drape for covering a surgical robot arm that includes a drive device for providing the drive to a surgical instrument. This drape comprises a cover for covering the robot arm to define a sterile boundary thereon and an interface element attached to the cover.

Patent Document 2 discloses a surgical robotic drape for covering a part of a surgical robot. This drape is configured to include a cover that covers the drive device of a surgical robot to define a sterile boundary thereon and a plurality of interface elements.

Patent Document 3 discloses a drape unit that, when a manipulator is connected to a drive unit, can maintain a state in which a clean area and an unclean area are isolated from each other even by the operation of the drive unit.

PRIOR ART DOCUMENTS

Patent Documents

[Patent Document 1] Japanese Translation of PCT International Application, No. 2018-515212
[Patent Document 2] Japanese Translation of PCT International Application, No. 2018-515213
[Patent Document 3] JP6138396B

SUMMARY OF THE INVENTION

Problems to be Solved by the Invention

The portion of a medical robot to which a surgical instrument is attached is provided with a movable member that transmits driving force to the surgical instrument and an opening that guides the movement of a movable member. If such an opening is provided between a clean area and an unclean area, the isolation between the clean area and the unclean area will be insufficient. In Patent Document 3, an adapter that covers such an opening is provided.

However, the opening for the forward/backward movement (linear movement) of the movable member is a long hole extending in the forward/backward direction, and an adapter that covers the entire opening is therefore provided also long. If such an adapter is exposed, it interferes with the movement of the movable member, and when some external force is applied to the adapter, unnecessary force is applied to the surgical instrument via the movable member, which may impair the accuracy and safety of treatment.

An object of the present invention is to provide a drape unit capable of sufficiently isolating a clean area and an unclean area from each other and improving the operability/safety of surgery.

Means for Solving the Problems

To solve the above problems, an aspect of the present invention provides a drape unit that is disposed between a medical robot holding a surgical instrument and the surgical instrument to isolate the surgical instrument and the medical robot from each other. The drape unit transmits power in a forward/backward direction from a power transmission part of the medical robot to a movable part provided in the surgical instrument. The drape unit comprises: a movable intervening part that receives the power from the power transmission part; and a fixed intervening part that is detachably attached to the medical robot. The fixed intervening part has a through-hole through which a part of the movable intervening part is inserted. The fixed intervening part has a housing portion that covers a part of the movable intervening part as viewed in a penetrating direction of the through-hole when the movable intervening part moves to an end portion in the forward/backward direction.

According to such a configuration, when the movable intervening part which closes the through-hole to prevent the exposure of an unclean area receives the power from the power transmission part to move to the end portion in the forward/backward direction, a part of the movable intervening part is covered with the housing portion of the fixed intervening part, and the exposure of the movable intervening part moving in the forward/backward direction can therefore be suppressed.

In the above drape unit, the movable intervening part may have: a first movable portion that receives the power from the power transmission part; a second movable portion that transmits the power to the movable part; and a third movable portion that extends from the second movable portion in the forward/backward direction, and the third movable portion may have a cover area that is housed in the housing portion. This allows the housing portion to house the cover area of the third movable portion extending in the forward/backward direction, and the third movable portion covers the through-hole and suppresses the exposure of the movable intervening part.

In the above drape unit, the fixed intervening part is preferably an assembly that comprises a first fixed portion provided with a first opening through which the first movable portion is inserted and a second fixed portion provided with a second opening through which the second movable portion is inserted, and the movable intervening part is preferably interposed between the first fixed portion and the second fixed portion and housed in the fixed intervening part so as not to drop off. This allows the movable intervening part to be interposed between the first fixed portion and the second fixed portion, and the movable intervening part is reliably prevented from dropping off from the fixed intervening part while suppressing the exposure of the movable intervening part.

In the above drape unit, a length of the second opening in the forward/backward direction is preferably shorter than a length of the first opening in the forward/backward direction. This allows the first opening to be covered in a region in which the second opening and the first opening do not overlap when viewed in the penetrating direction, so that the through-hole is less likely to occur even when the third movable portion moves in the forward/backward direction, and the exposure of an unclean area is suppressed.

In the above drape unit, the fixed intervening part may have a guide groove that receives a part of the movable intervening part and guides the movable intervening part to move in the forward/backward direction, and in a state in which the drape unit and the surgical instrument are mounted on the medical robot, when viewed in the penetrating direction, predetermined gaps may be provided between the third movable portion and the first fixed portion and between the third movable portion and the second fixed portion. The presence of the above gaps can reduce the possibility of occurrence of a problem in that, when the movable part of the surgical instrument attached to the medical robot is being moved, the fixed intervening part and the movable intervening part collide with each other to lock the movable part.

In the above drape unit, the second opening may be closed by the third movable portion. This allows the third movable portion to cover the second opening, and the exposure of an unclean area is suppressed.

In the above drape unit, a length of the third movable portion in the forward/backward direction is preferably longer than a length of the second opening in the forward/backward direction. This allows the second opening to be covered even when the third movable portion moves in the forward/backward direction, and the exposure of an unclean area is suppressed.

In the above drape unit, in a state before the surgical instrument is mounted on the medical robot, the movable intervening part is preferably disposed so as to close the entire first opening of the fixed intervening part mounted on the surgical instrument. This allows the movable intervening part to close the entire first opening even when the surgical instrument is not mounted on the medical robot, and the exposure of an unclean area is suppressed.

In the above drape unit, the movable intervening part may be configured so as not to come into contact with an inner wall surface that constitutes the through-hole of the fixed intervening part, in a state in which the movable intervening part is located at the end portion in the forward/backward direction. This can alleviate the force applied to the surgical instrument from the movable intervening part when the movable intervening part stops at the movable range end portion.

In the above drape unit, a plurality of the movable intervening parts may be arranged in parallel in a direction orthogonal to the forward/backward direction and the penetrating direction. Through this configuration, even when a plurality of movable intervening parts is provided, interference between the movable intervening parts and exposure of the movable intervening parts are suppressed.

Effect of the Invention

According to the present invention, there can be provided a drape unit capable of sufficiently isolating a clean area and an unclean area from each other and improving the operability/safety of surgery.

BRIEF DESCRIPTION OF DRAWINGS

FIG. 10 is a perspective view for exemplifying guide grooves of the fixed intervening part.

EMBODIMENTS FOR CARRYING OUT THE INVENTION

Figure 1:
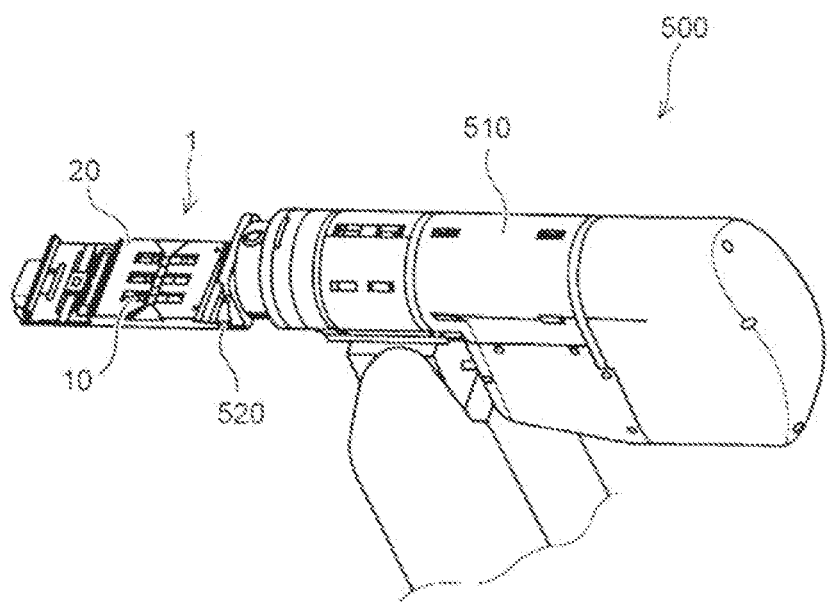
FIG. 1 is a perspective view for exemplifying a drape unit according to an embodiment of the present invention.
Figure 1:
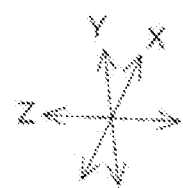

Hereinafter, embodiments of the present invention will be described with reference to the drawings. In the following description, the same members are denoted by the same reference numerals and the description of members once explained may be omitted.

(Configuration of Medical Robot and Drape Unit)

FIG. 1 is a perspective view for exemplifying a drape unit according to an embodiment of the present invention.

Figure 2:
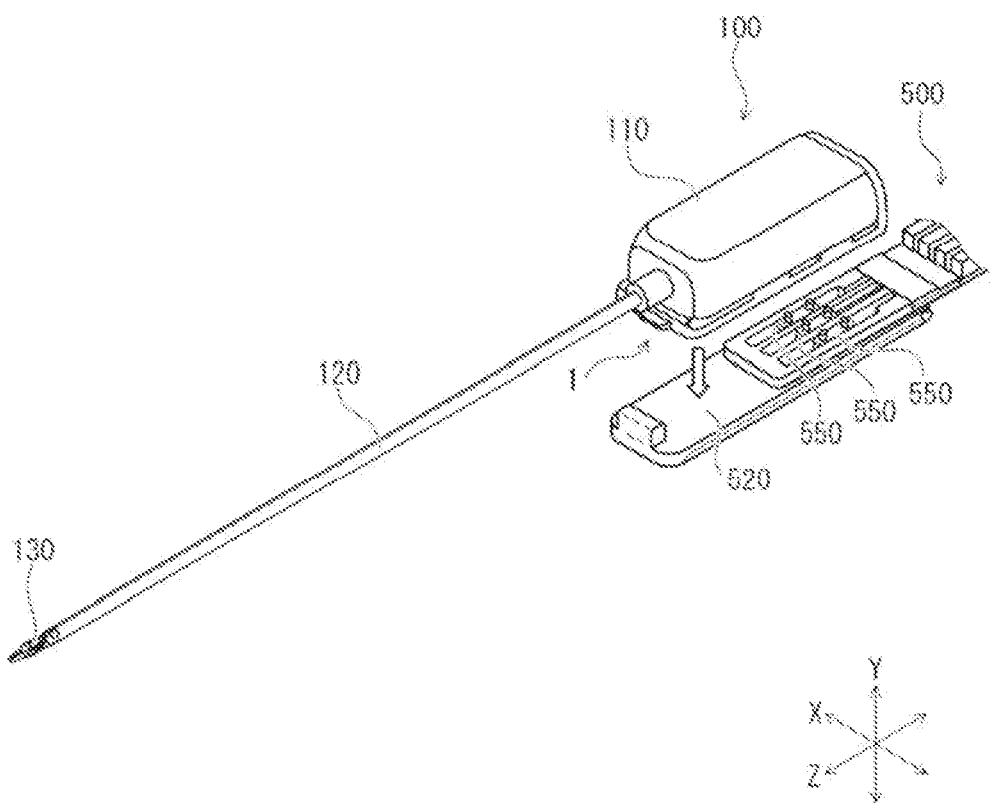
FIG. 2 is a perspective view for exemplifying the mounting state of a surgical instrument.

FIG. 2 is a perspective view for exemplifying the mounting state of a surgical instrument.

Figure 3:
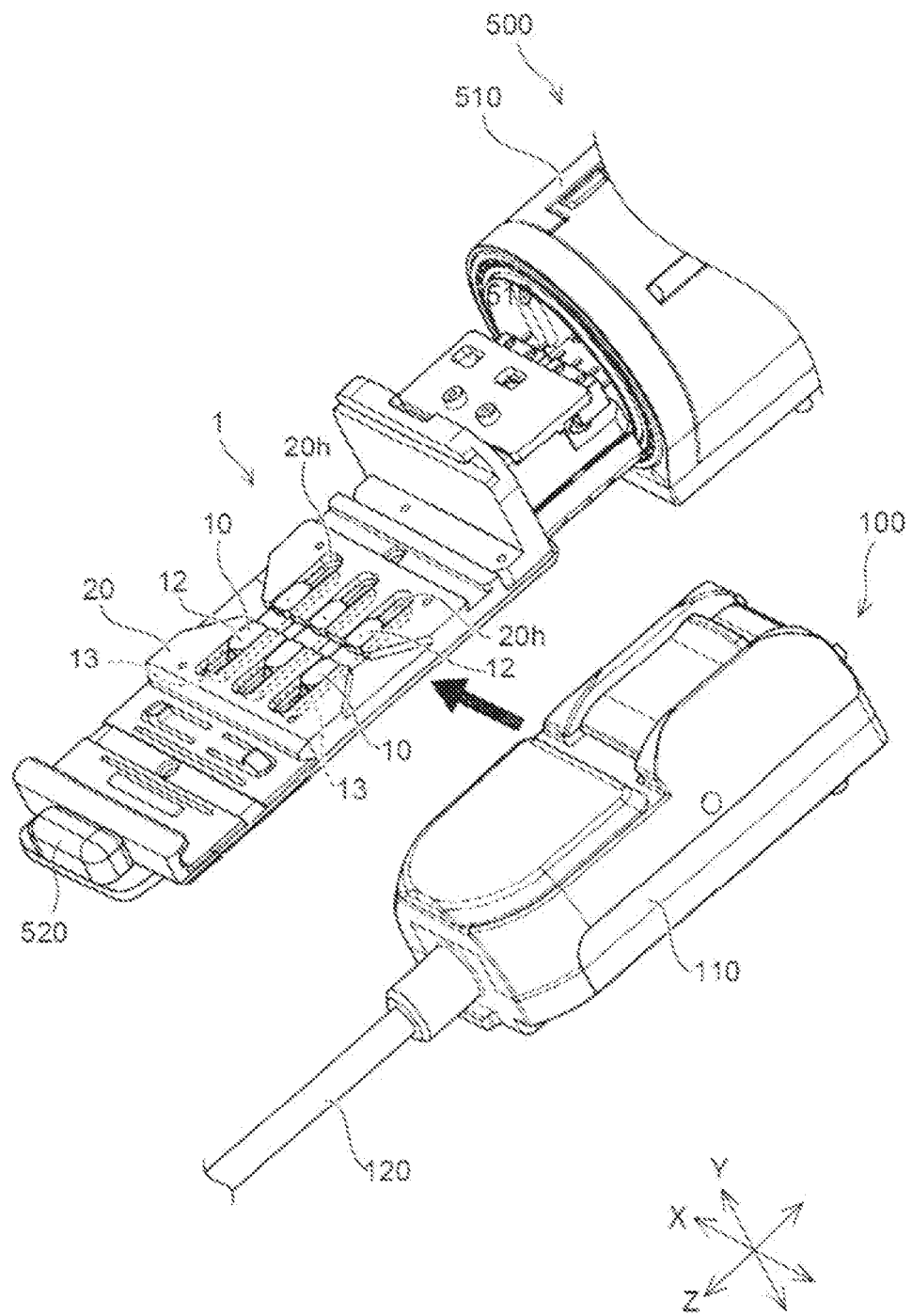
FIG. 3 is a perspective view for exemplifying attachment of the surgical instrument to the drape unit.

FIG. 3 is a perspective view for exemplifying attachment of the surgical instrument to the drape unit.

Figure 4:
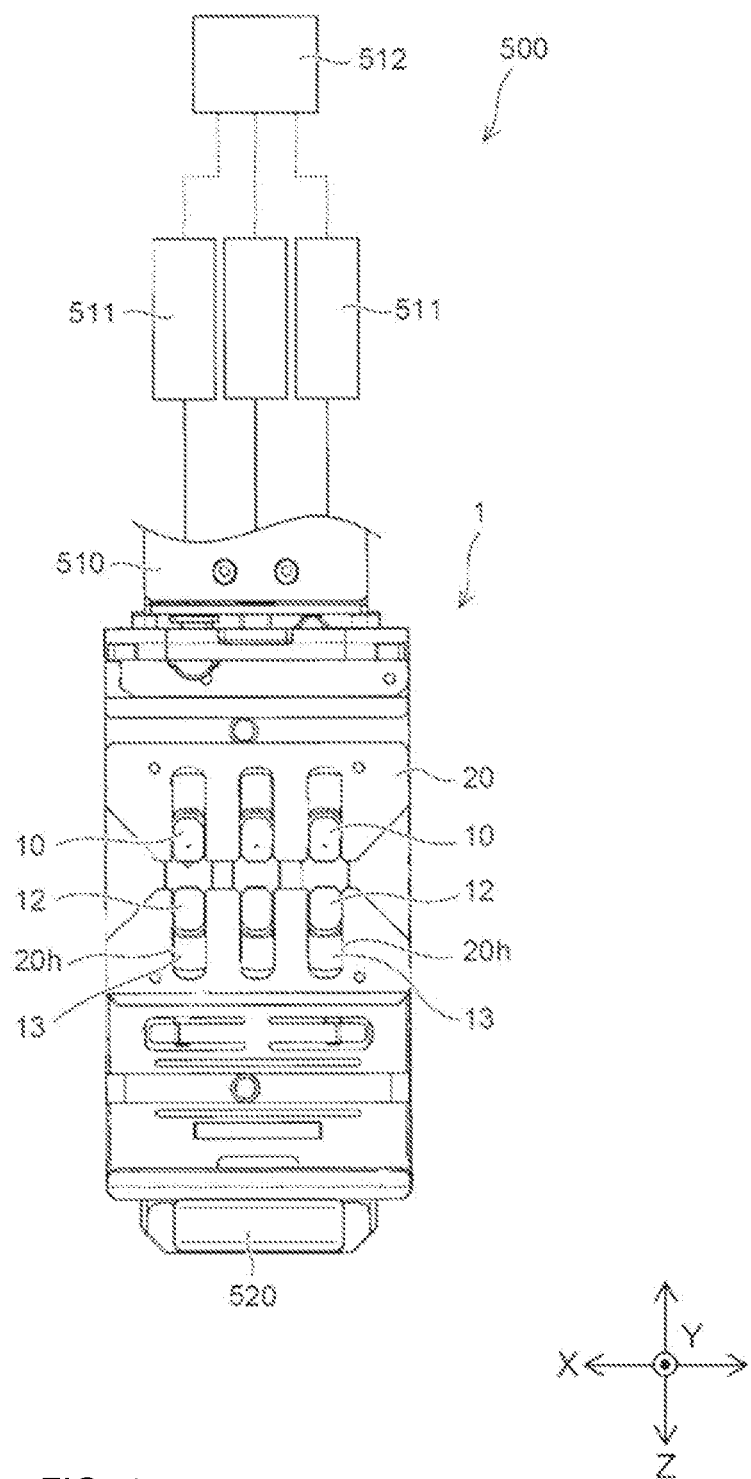
FIG. 4 is a plan view for exemplifying a driving portion of a medical robot.

FIG. 4 is a plan view for exemplifying a driving portion of a medical robot.

As illustrated in FIGS. 1 and 2, a medical robot 500 has a multi-degree-of-freedom arm 510 that is a manipulator capable of being remotely controlled. The tip portion of the multi-degree-of-freedom arm 510 is provided with a mounting portion 520 to which a drape unit 1 according to the present embodiment is attached. A surgical instrument 100 is attached to the multi-degree-of-freedom arm 510 via the drape unit 1.

The drape unit 1 according to the present embodiment is detachably attached to the mounting portion 520 of the multi-degree-of-freedom arm 510, and the surgical instrument 100 is detachably attached to the drape unit 1. This allows the drape unit 1 to be disposed between the medical robot 500, which holds the surgical instrument 100, and the surgical instrument 100, and the drape unit 1 serves to isolate the surgical instrument 100 and the medical robot 500 from each other. The drape unit 1 also serves to transmit power in the forward/backward direction from power transmission parts 550 of the medical robot 500 to respective movable parts 150 provided in the surgical instrument 100.

Here, in the present embodiment, the direction (forward/backward direction) of the power transmitted from the power transmission parts 550 to the drape unit 1 will be referred to as a Z direction, one of the directions orthogonal to the Z direction will be referred to as an X direction, and the direction orthogonal to the Z direction and the X direction will be referred to as a Y direction.

In the present embodiment, the Z direction is also the direction in which the tip portion of the multi-degree-of-freedom arm 510 extends. The tip portion (mounting portion 520) of the multi-degree-of-freedom arm 510 is configured to rotate about an axis in the Z direction. The arm portion of the multi-degree-of-freedom arm 510 is also axially rotatable. The surgical instrument 100 attached to the medical robot 500 can therefore approach a patient from various angles using the multi-degree-of-freedom arm 510.

As illustrated in FIG. 2, the surgical instrument 100 comprises a main body 110, a shaft 120 extending from the main body 110, and a treatment part 130 provided at the tip of the shaft 120 (an end portion opposite to the main body 110). The treatment part 130 is, for example, forceps. For easy understanding of the relationships between the surgical instrument 100 and drape unit 1 and the mounting portion 520 of the medical robot 500, FIG. 2 illustrates a situation in which the drape unit 1 in a state of being mounted on the surgical instrument 100 is mounted on the mounting portion 520 of the medical robot 500. At the time of actual treatment, as illustrated in FIG. 3, the drape unit 1 is first mounted on the mounting portion 520 of the medical robot 500, and the surgical instrument 100 is then attached to the drape unit 1 which has been mounted on the mounting portion 520.

As illustrated in FIGS. 3 and 4, the medical robot 500 is provided with actuator parts 511 and a control part 512. The actuator parts 511 generate driving force for operating the surgical instrument 100. The actuator parts 511 are connected to respective power transmission parts 550 (see FIG. 5) that transmit driving force in the forward/backward direction (Z direction) to the drape unit 1.

The present embodiment will be described as being applied to an example in which the actuator parts 511 generate driving force using a gas such as air or a fluid. The actuator parts 511 may use electric motors, and the type of generating the power is not limited. The actuator parts 511 may have a configuration using a piston and a cylinder or a configuration in which the driving force is generated from other known fluids, and the specific configuration is not limited.

The control part 512 controls generation of the driving force in the actuator parts 511. The control part 512 also controls the movement in the Z direction in the power transmission parts 550 and the arrangement positions of the power transmission parts 550. The present embodiment will be described as being applied to an example in which the control part 512 controls the supply of a gas such as air to the actuator parts 511.

To attach the surgical instrument 100 to the multi-degree-of-freedom arm 510, the main body 110 of the surgical instrument 100 is fitted into the drape unit 1, which has been attached to the mounting portion 520 of the multi-degree-of-freedom arm 510, so as to be slid, for example, in the X direction.

By fitting the main body 110 into the drape unit 1, the power from the power transmission parts 550 can be transmitted to the main body 110 via the drape unit 1. Link means (e.g., wires) that transmit power to the treatment part 130 are provided in the main body 110, and the movement of the power transmission parts 550 can be transmitted from the drape unit 1 to the link means of the surgical instrument 100 to operate the treatment part 130.

The surgical instrument 100 to be attached to the medical robot 500 is sterilized and placed in a clean area. On the other hand, the medical robot 500 is placed in an unclean area that is not as clean as the surgical instrument 100. The drape unit 1, which zones a clean area and an unclean area, includes a membrane-like drape (not illustrated). The drape unit 1 is also sterilized.

(Detailed Structure of Drape Unit)

Figure 5:
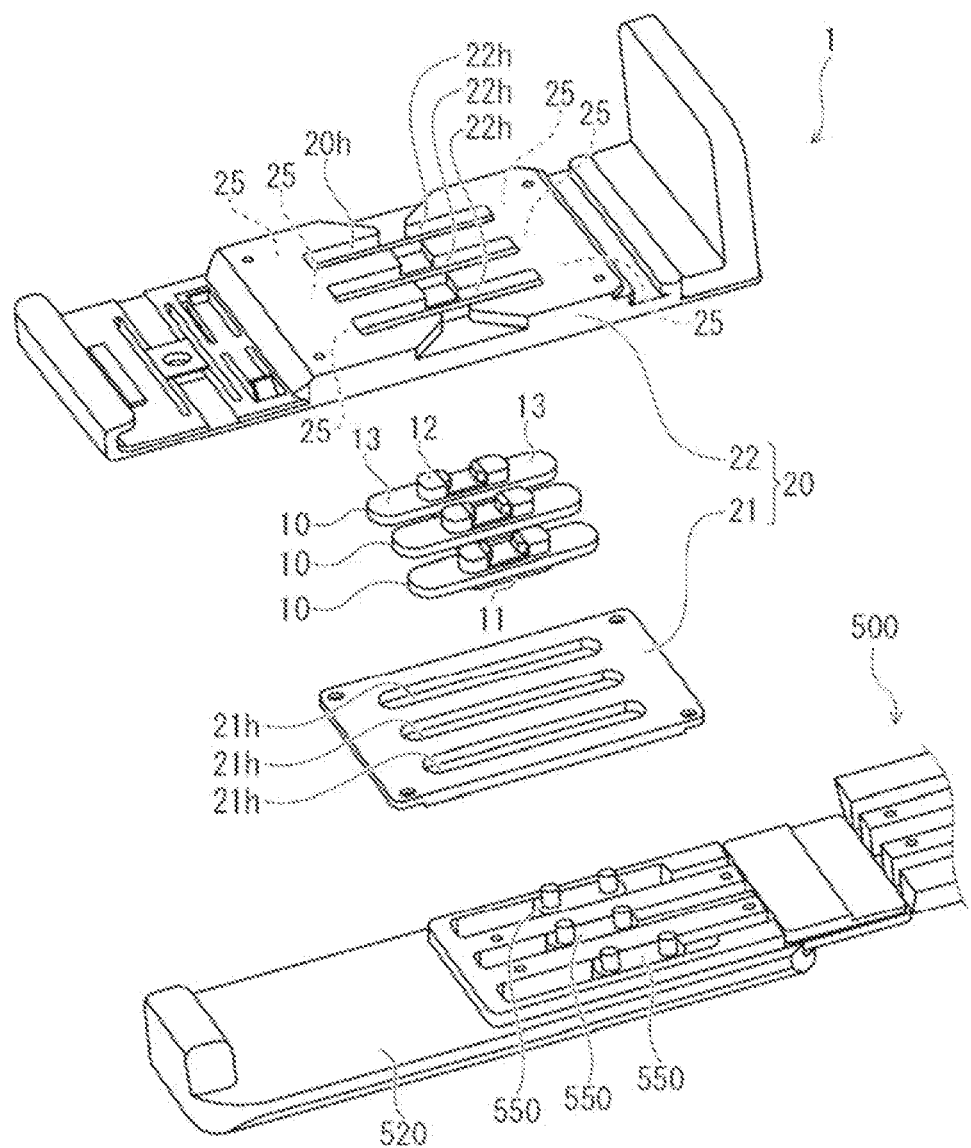
FIG. 5 is an exploded perspective view of the drape unit according to the present embodiment.

FIG. 5 is an exploded perspective view of the drape unit according to the present embodiment.

Figure 6:
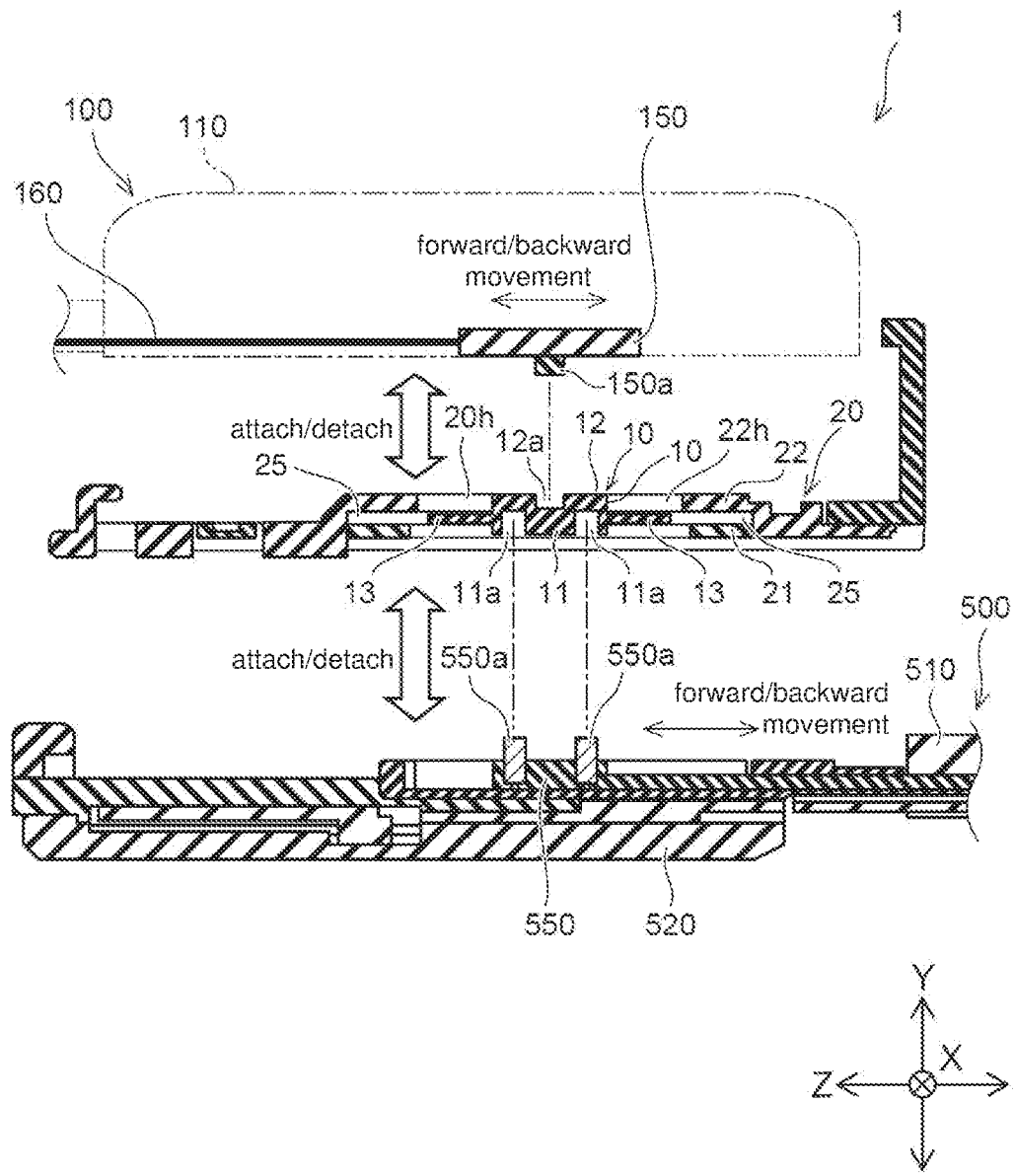
FIG. 6 is a cross-sectional view for exemplifying the configuration of the drape unit according to the present embodiment.

FIG. 6 is a cross-sectional view for exemplifying the configuration of the drape unit according to the present embodiment.

FIG. 6 illustrates a ZY cross section of the drape unit 1. For descriptive purposes, FIG. 6 illustrates not only the cross-sectional view of the drape unit 1 but also cross-sectional views of a power transmission part 550 of the medical robot 500 and a movable part 150 of the surgical instrument 100 that are in a state of being separated from the drape unit 1.

As illustrated in FIGS. 5 and 6, the drape unit 1 includes movable intervening parts 10 that receive the power from the power transmission parts 550 of the medical robot 500 and a fixed intervening part 20 that is detachably attached to the medical robot 500. The fixed intervening part 20 has through-holes 20h through which respective parts of the movable intervening parts 10 are inserted.

The fixed intervening part 20 is an assembly that comprises a first fixed portion 21 and a second fixed portion 22. The movable intervening parts 10 are arranged so as to be interposed between the first fixed portion 21 and the second fixed portion 22 and are housed so as not to drop off from the fixed intervening part 20.

The fixed intervening part 20 has housing portions 25 that cover respective parts of the movable intervening parts 10 as viewed in the penetrating direction (Y direction) of the through-holes 20h when the movable intervening parts 10 move to end portions (movable range ends) in the forward/backward direction. That is, the housing portions 25 of the fixed intervening part 20 are configured to house respective parts of the movable intervening parts 10 when the movable intervening parts 10 move to the movable range ends in the Z direction, and the exposure of the movable intervening parts 10 to the outside is therefore suppressed. In particular, when the surgical instrument 100 is replaced during surgery, the drape unit 1 is in a state of being exposed from when the surgical instrument 100 mounted on the medical robot 500 is removed to when another surgical instrument 100 is attached. At this time, there is a risk that the practitioner or an assistant (supporting staff) may carelessly touch the drape unit 1 or some entity (e.g., a robot arm disposed next to the drape unit 1) may collide with the drape unit 1. In the medical robot 500 according to the present embodiment, as described above, the movable range ends of the movable intervening parts 10 of the drape unit 1 in the Z direction are housed in the housing portions 25 of the fixed intervening parts 20, and therefore problems are less likely to occur, such as unexpected movement, dropping, and damage of the movable intervening parts 10 due to contact and/or collision.

As disclosed in Patent Document 3, for example, in the case of a configuration in which a manipulator is provided on a base that is fixedly disposed, if an adapter is placed on the drape body, the entire opening can be covered with the adapter. On the other hand, in the case of the drape unit 1 provided on the medical robot 500 as in the present embodiment, the unit provided with the power transmission parts 550 freely rotates and moves, and the through-holes 20h of the drape unit 1 face various directions accordingly. Therefore, if a configuration in which the adapter is simply placed as in Patent Document 3 is employed, the movable intervening parts 10 may drop off during the operation of the medical robot 500. Fortunately, in the drape unit 1 according to the present embodiment, the movable intervening parts 10 are housed in the fixed intervening part 20 so as not to drop off, and therefore even when the through-holes 20h of the drape unit 1 face any direction, the movable intervening parts 10 can appropriately prevent the exposure of an unclean area.

(Detailed Structure of Movable Intervening Parts)

Each movable intervening part 10 has a first movable portion 11 that receives power from the corresponding power transmission part 550, a second movable portion 12 that transmits power to the corresponding movable part 150 of the surgical instrument 100, and a third movable portion 13 that extends from the second movable portion 12 in the forward/backward direction (Z direction).

The first movable portion 11 is provided with recessed portions 11a into which protruding portions 550a of the power transmission part 550 are fitted. When the drape unit 1 is attached to the mounting portion 520 of the multi-degree-of-freedom arm 510, the protruding portions 550a of the power transmission part 550 are fitted into the recessed portions 11a of the first movable portion 11 of the movable intervening part 10. This allows the power when the power transmission part 550 moves forward/backward to be transmitted to the first movable portion 11, and the movable intervening part 10 can move forward/backward.

The second movable portion 12 is provided with a recessed portion 12a into which a protruding portion 150a of the movable part 150 of the surgical instrument 100 is fitted. When the main body 110 of the surgical instrument 100 is attached to the drape unit 1, the protruding portion 150a protruding from the back surface of the movable part 150 is fitted into the recessed portion 12a of the second movable portion 12. This allows the movable intervening part 10 and the movable part 150 of the surgical instrument 100 to be engaged with each other, and the forward/backward movement of the power transmission part 550 can be transmitted from the movable intervening part 10 to the movable part 150 of the surgical instrument 100. That is, when the power transmission part 550 is moved forward/backward, the power is transmitted from the movable intervening part 10 to the movable part 150, and the forward/backward movement of the movable part 150 can be transmitted to a wire 160 to operate the treatment part 130 via the wire W.

The third movable portion 13 is a portion that extends from the second movable portion 12 in the Z direction (forward/backward direction). When viewed in the Y direction, the third movable portion 13 is provided larger than the second movable portion 12 and therefore serves to cover the through-hole 20h.

(Detailed Structure of Fixed Intervening Part)

The first fixed portion 21 is provided with first openings 21h through which the first movable portions 11 of the movable intervening parts 10 are inserted, and the second fixed portion 22 is provided with second openings 22h through which the second movable portions 12 of the movable intervening parts 10 are inserted. The first openings 21h and the second openings 22h are elongated holes extending in the Z direction and guide the movable intervening parts 10 to move forward/backward in the Z direction within the range of the elongated holes.

That is, the movable intervening parts 10 can move forward/backward in the Z direction within the range of the elongated holes of the first openings 21h and the second openings 22h. In the movable regions of the movable intervening parts 10 between the first fixed portion 21 and the second fixed portion 22, portions that overlap the first fixed portion 21 as viewed in the Y direction are the housing portions 25.

(Positional Relationship Between Movable Intervening Part and Fixed Intervening Part)

Figure 7A:
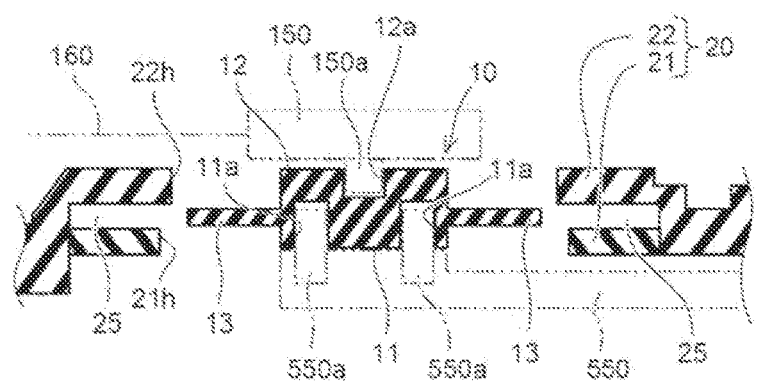
FIGS. 7A and 7B are schematic views for exemplifying a movable intervening part and a fixed intervening part.
Figure 7B:
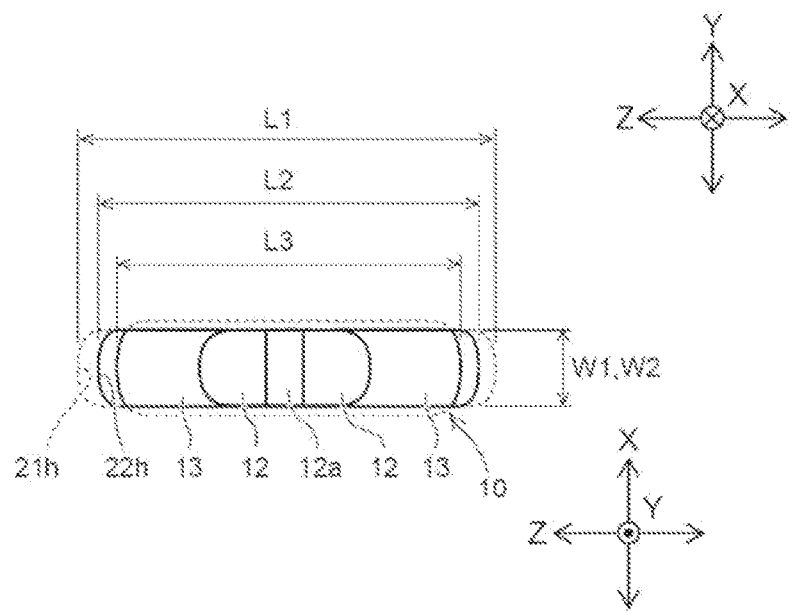

FIGS. 7A and 7B are schematic views for exemplifying a movable intervening part and a fixed intervening part.

FIG. 7A illustrates a schematic cross-sectional view of a movable intervening part 10 and the fixed intervening part 20, and FIG. 7B illustrates a schematic plan view illustrating the positional relationship between the movable intervening part 10 and the corresponding through-hole 20h.

As illustrated in FIG. 7B, when viewed in the X direction, the movable intervening part 10 preferably does not protrude from the fixed intervening part 20 in the Y direction. Additionally or alternatively, the engagement between the second movable portion 12 and the movable part 150 of the surgical instrument 100 is preferably fitting between the protruding portion 150a provided on the movable part 150 and the recessed portion 12a provided in the second movable portion 12. This allows the movable intervening part 10 to be housed in the fixed intervening part 20, and no portion protrudes outward from the fixed intervening part 20. Therefore, even if the drape unit 1 is exposed before the surgical instrument 100 is attached or when the surgical instrument 100 is replaced, a situation in which the movable intervening part 10 is carelessly touched is unlikely to occur.

In particular, when the movable intervening part 10 moves forward/backward (linear movement), the exposed area of the movable intervening part 10 tends to be wide because the moving stroke is long. Therefore, the possibility that the movable intervening part 10 is carelessly touched is high. As described above, the movable intervening part 10 is housed in the fixed intervening part 20, so that even when the movable intervening part 10 is exposed, it is not easily touched because there is no protrusion. This enables safe and quick attachment and replacement of the surgical instrument 100.

As illustrated in FIG. 7B, the third movable portion 13 of the movable intervening part 10 is provided so as to extend from the second movable portion 12 in the Z direction (forward/backward direction) and therefore almost closes the second opening 22h when viewed in the Y direction. The second opening 22h is almost closed by the third movable portion 13, so that the through-hole 20h is less likely to occur even when the third movable portion 13 moves forward/backward in the Z direction. Through this configuration, in the drape unit 1 provided between a clean area and an unclean area, the exposure of the unclean area due to the occurrence of the through-hole 20h is suppressed.

The width (length in the X direction) W2 of the second opening 22h is equivalent to the width W1 of the first opening 21h, but the length L2 of the second opening 22h in the Z direction is preferably shorter than the length L1 of the first opening 21h in the Z direction. The center of the second opening 22h approximately coincides with the center of the first opening 21h. When viewed in the Y direction, therefore, the edge of the second opening 22h in the Z direction is located inside the edge of the first opening 21h in the Z direction.

This allows the first opening 21h to be covered in a region in which the second opening 22h and the first opening 21h do not overlap when viewed in the Y direction. Therefore, even when the third movable portion 13 moves forward/backward in the Z direction, the substantially opening area of the through-hole 20h is less likely to expand, and the exposure of an unclean area is suppressed.

The length L3 of the third movable portion 13 in the Z direction may be made longer than the length L2 of the second opening 22h in the Z direction. This allows the third movable portion 13 to cover the entire second opening 22h when viewed in the Y direction.

In this case, by adjusting the length L3 of the third movable portion 13 in the Z direction and the length of the housing portion 25 in the Z direction, the entire second opening 22h may be covered with the third movable portion 13 regardless of the position of the movable intervening part 10 within the movable range, or the entire second opening 22h may be covered with the third movable portion 13 when the movable intervening part 10 is located within a part of the movable range. This increases the area in which the second opening 22h is almost closed by the movable intervening part 10, and the exposure of an unclean area is effectively suppressed.

(Movement of Movable Intervening Part)

FIGS. 8A to 8D are schematic views for exemplifying the movement of the movable intervening part.

Figure 8A:
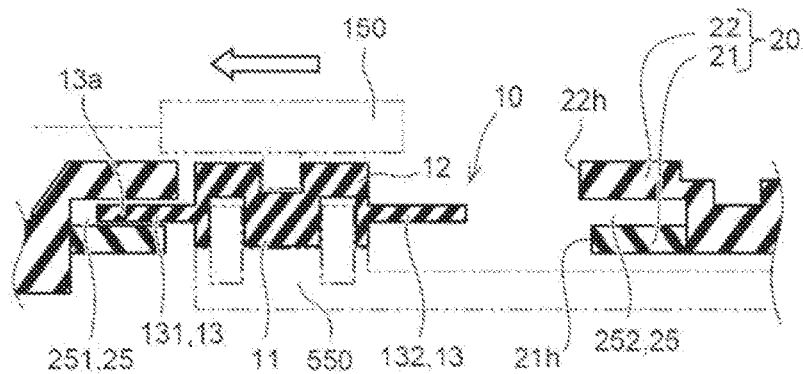
FIGS. 8A and 8D are schematic views for exemplifying the movement of the movable intervening part.
Figure 8B:
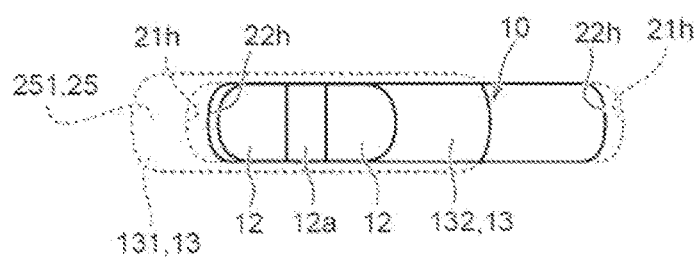

FIG. 8A illustrates a schematic cross-sectional view when a movable intervening part 10 moves to one end, and FIG. 8B illustrates a schematic plan view illustrating the positional relationship between the movable intervening part 10 and the corresponding through-hole 20h when the movable intervening part 10 moves to the one end.

Figure 8C:
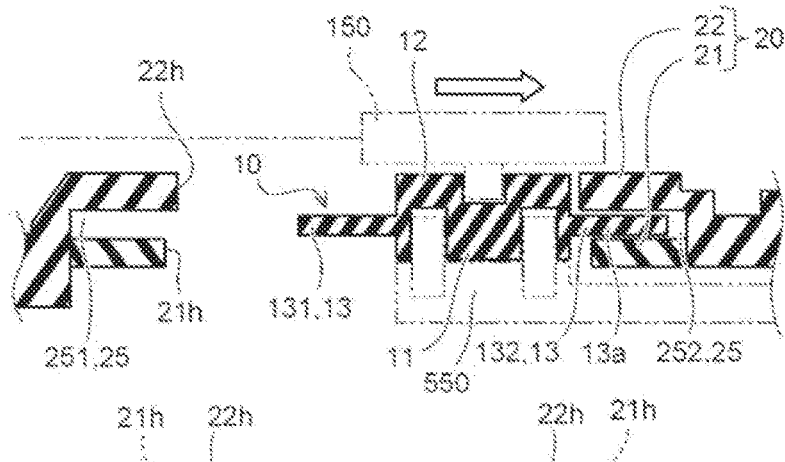
Figure 8D:
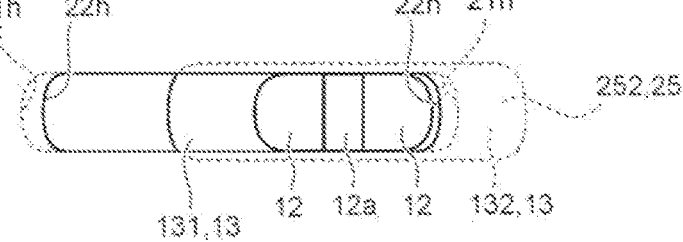

FIG. 8C illustrates a schematic cross-sectional view when the movable intervening part 10 moves to the other end, and FIG. 8D illustrates a schematic plan view illustrating the positional relationship between the movable intervening part 10 and the corresponding through-hole 20h when the movable intervening part 10 moves to the other end.

As illustrated in FIGS. 8A and 8B, when the movable intervening part 10 moves to the one end, a third movable portion 131 extending to the one end side of the movable intervening part 10 is housed in a housing portion 251 on the one end side.

On the other hand, as illustrated in FIGS. 8C and 8D, when the movable intervening part 10 moves to the other end, a third movable portion 132 extending to the other end side of the movable intervening part 10 is housed in a housing portion 252 on the other end side.

A portion of the third movable portion 131, 132 housed in the housing portion 251, 252 is a cover area 13a. The cover area 13a of the third movable portion 131, 132 is housed in the housing portion 251, 252 in the forward/backward movement of the movable intervening part 10, and the movable intervening part 10 (third movable portion 13) can thereby cover the through-hole 20h without exposing the end portion of the movable intervening part 10 in the forward/backward direction (end portion of the third movable portion 131, 132) to external.

As illustrated in FIGS. 8A and 8B, the movable intervening part 10 may be configured so as not to come into contact with the inner wall surface, which constitutes the through-hole 20h of the fixed intervening part 20, in a state in which the movable intervening part 10 is located on each of the one end side and the other end side in the Z direction.

For example, the movable intervening part 10 is configured such that when it is moved through the drive control of the corresponding actuator part 511 by the control part 512, the movable end of the movable intervening part 10 is stopped before coming into contact with the inner wall surface of the through-hole 20h. Through this configuration, when the movable intervening part 10 stops at each of the movable range ends on the one end side and the other end side, sudden force generated due to collision with the inner wall surface (impact force due to collision) can be prevented from being applied to the surgical instrument 100 from the movable intervening part 10.

Alternatively, the movable intervening part 10 may be configured such that when it moves to the movable range end, the movable intervening part 10 is brought into contact with the inner wall surface of the through-hole 20h to serve as a stopper for the movable range. Through this configuration, when force is applied from the surgical instrument 100 side in a state in which the movable intervening part 10 is located at the movable range end, the contact between the movable intervening part 10 and the inner wall surface of the through-hole 20h can receive that force to alleviate the impact transmitted to the power transmission part 550.

(Example of Plurality of Movable Intervening Parts)

Figure 9:
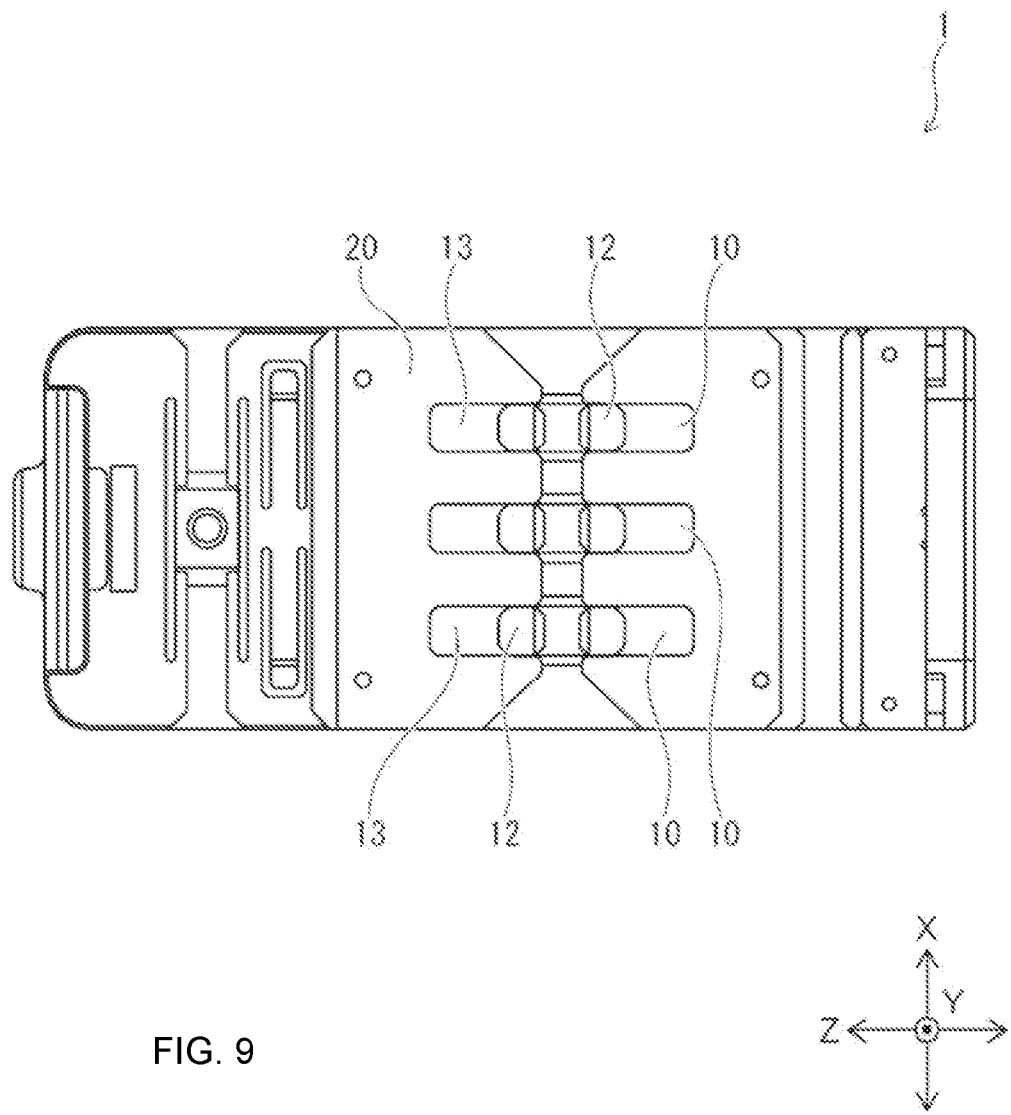
FIG. 9 is a plan view of the drape unit.

FIG. 9 is a plan view of the drape unit.

In the drape unit 1 illustrated in FIG. 9, a plurality of movable intervening parts 10 is arranged in parallel in the X direction. In the present embodiment, three movable intervening parts 10 are provided in parallel. The fixed intervening part 20 is provided with a plurality of through-holes 20h corresponding to the movable intervening parts 10. The movable intervening parts 10 can move forward/backward independently of each other. The movable intervening parts 10 are driven independently without interfering with each other, and the operability of the surgical instrument 100 can therefore be improved.

The movable ranges of the movable intervening parts 10 may be the same or may otherwise be different from each other. According to the configuration of the present embodiment, even when a plurality of movable intervening parts 10 is provided, interference between the movable intervening parts 10 and exposure of the movable intervening parts 10 are suppressed.

FIG. 10 is a perspective view for exemplifying guide grooves of the fixed intervening part.

FIG. 10 illustrates a perspective view of the second fixed portion 22 of the fixed intervening part 20 when viewed from the inside (movable intervening part 10 side).

The second fixed portion 22 of the fixed intervening part 20 may be provided with guide grooves 225 that each receive a part of the movable intervening part 10 and guides the movable intervening part 10 to move in the Z direction. Each guide groove 225 is a spot facing portion provided outside the edge of the second opening 22h. The third movable portion 13 of the movable intervening part 10 is fitted in the guide groove 225 so as to be able to move forward/backward.

The guide groove 225 is provided to have a width (length in the X direction) approximately equal to or slightly wider than the width (length in the X direction) of the third movable portion 13 and a length (length in the Z direction) longer than the length (the length in the Z direction) of the second opening 22h.

The third movable portion 13 is provided in a flange shape that projects in each of the length direction (Z direction) and the width direction (X direction) with respect to the second movable portion 12 which is inserted through the second opening 22h. Therefore, when the second movable portion 12 is inserted through the second opening 22h, the third movable portion 13 does not get out of the second opening 22h.

The position of the third movable portion 13 in the X direction is restricted by walls 225a facing each other in the width direction (X direction) of the guide groove 225. On the other hand, the position of the third movable portion 13 in the Z direction is movable in the length direction (Z direction) of the guide groove 225. The movable intervening part 10 can therefore move in the Z direction along the guide groove 225 while being restricted in the X direction by the guide groove 225.

Even the second movable portion 12 inserted through the second opening 22h and the first movable portion 11 inserted through the first opening 21h can each serve as a guide that allows the movable intervening part 10 to move in the Z direction while restricting the position of the movable intervening part 10 in the X direction, but the third movable portion 13 can perform stable guide by being in long contact with the walls 225a of the guide groove in the Z direction because the third movable portion 13 is provided longer than the first movable portion 11 and the second movable portion 12 in the Z direction.

When a plurality of second openings 22h is provided to correspond to a plurality of movable intervening parts 10 and the guide grooves 225 are provided to correspond to respective second openings 22h, the walls 225a are provided between adjacent guide grooves 225. The walls 225a provide partitions between the adjacent movable intervening parts 10, and it is possible to prevent the adjacent movable intervening parts 10 from interfering with each other. Moreover, the presence of the walls 225a allows the spaces beside the third movable portions 13 to be partitioned, and the exposure of an unclean area can thereby be easily suppressed.

Additionally or alternatively, in a state in which the drape unit 1 and the surgical instrument 100 are mounted on the medical robot 500, when viewed in the Y direction, predetermined gaps may be provided between the third movable portion 13 and the first fixed portion 21 and between the third movable portion 13 and the second fixed portion 22.

The presence of such gaps as the above can reduce the possibility of occurrence of a problem in that, when the movable part 150 of the surgical instrument 100 attached to the medical robot 500 is being moved, the fixed intervening part 20 and the movable intervening part 10 collide with each other to lock the movable part 150.

Another Embodiment

Figure 11A:
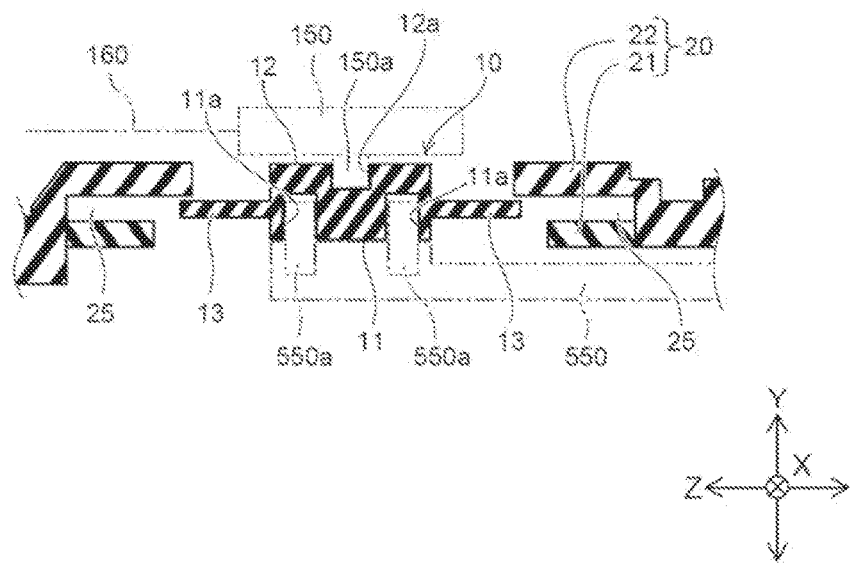
FIGS. 11A and 11B are schematic views for exemplifying the configuration of another movable intervening part.
Figure 11B:
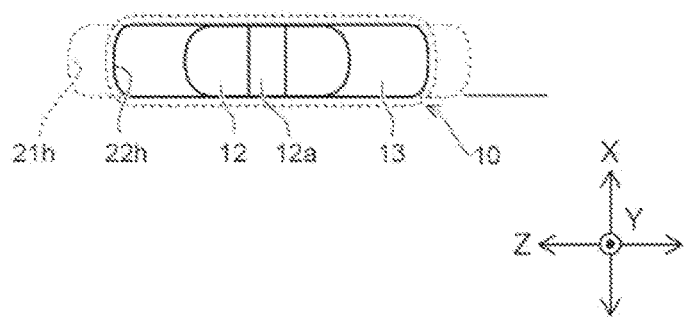

FIGS. 11A and 11B are schematic views for exemplifying the configuration of another movable intervening part. FIG. 11A illustrates a schematic cross-sectional view of a movable intervening part 10 and a fixed intervening part 20, and FIG. 11B is a schematic plan view illustrating the positional relationship between the movable intervening part 10 and a through-hole 20h.

The third movable portion 13 of the movable intervening part 10 illustrated in FIGS. 11A and 11B is provided so as to cover the entire second opening 22h. This allows the movable intervening part 10 to close the entire second opening 22h even when the surgical instrument 100 is not mounted on the medical robot 500, and an unclean area is less likely to be exposed.

Figure 12A:
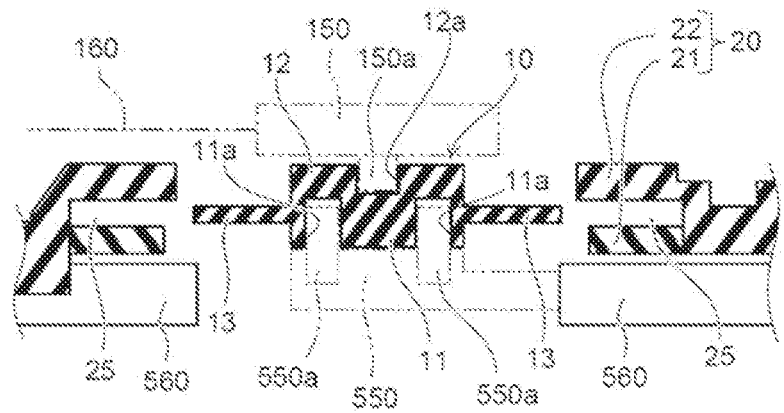
FIGS. 12A and 12C are schematic cross-sectional views illustrating an example of stoppers.
Figure 12B:
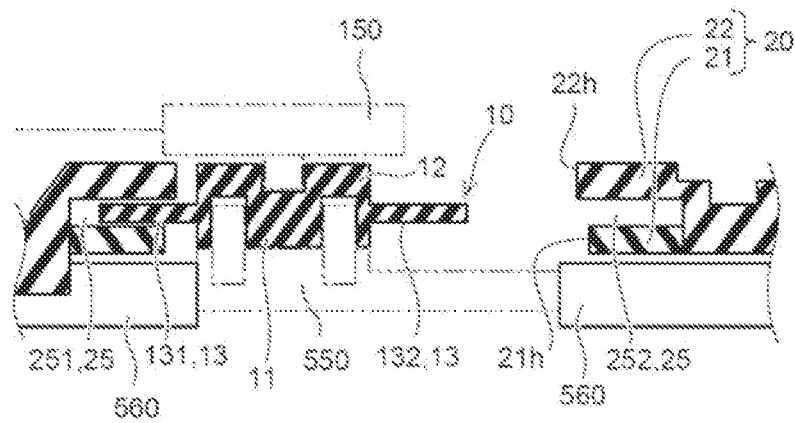
Figure 12C:
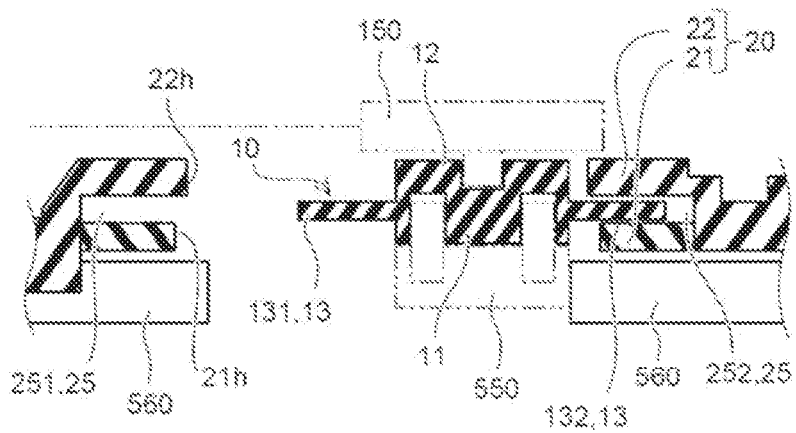

FIGS. 12A to 12C are schematic cross-sectional views illustrating an example of stoppers.

This example is provided with stoppers 56 with which the power transmission part 550 comes into contact when the movable intervening part 10 reaches the movable range ends of the movable range. The stoppers 560 may be provided on the mounting portion 520 of the multi-degree-of-freedom arm 510 or may otherwise be provided on the fixed intervening part 20.

When the movable intervening part 10 moves from an intermediate position illustrated in FIG. 12A to one end side illustrated in FIG. 12B and reaches the movable range end, the power transmission part 550 comes into contact with the corresponding stopper 560. This allows the movable intervening part 10 to stop at the one end of the movable range.

On the other hand, when the movable intervening part 10 moves to the other end side illustrated in FIG. 12C and reaches the movable range end, the power transmission part 550 comes into contact with the corresponding stopper 560. This allows the movable intervening part 10 to stop at the other end of the movable range.

A material or structure having a higher cushioning action than that of the fixed intervening part 20 may be used as each stopper 560. This can alleviate the reaction force at the time of collision when the movable intervening part 10 comes into contact with the stopper 560 rather than when coming into contact with the fixed intervening part 20.

Thus, according to the present embodiment, there can be provided a drape unit 1 capable of sufficiently isolating a clean area and an unclean area from each other and improving the operability of surgery. In particular, when the movable intervening part 10 moves forward/backward (linear movement), each through-hole 20h expands also in the forward/backward direction, but by reliably covering the through-hole 20h with the movable intervening part 10 as in the present embodiment, a clean area and an unclean area can be reliably isolated from each other. Moreover, the movable intervening part 10 is housed in the fixed intervening part 20; therefore, the exposure of the movable intervening part 10 is suppressed, and the surgical instrument 100 can be safely and quickly attached and replaced.

Although the present embodiments have been described above, the present invention is not limited to these examples. For example, in the above embodiments, an example in which three movable intervening parts 10 are arranged in parallel has been described, but the number of the movable intervening parts 10 is not limited. Moreover, an example of the forceps has been described as the treatment part 130 of the surgical instrument 100, but a treatment part 130 other than the forceps may be employed. Furthermore, the scope of the present invention encompasses those to which a person skilled in the art appropriately makes addition or removal of constitutional elements or design changes with respect to the previously-described embodiments or specific examples and those in which features of the embodiments are appropriately combined, provided that they have the subject matters of the present invention.

DESCRIPTION OF REFERENCE NUMERALS

1 Drape unit
10 Movable intervening part
11 First movable portion
11a Recessed portion
12 Second movable portion
12a Recessed portion
13, 131, 132 Third movable portion 13a Cover area
20 Fixed intervening part
20h Through-hole
21 First fixed portion
21h First opening
22 Second fixed portion
22h Second opening
25, 251, 252 Housing portion
100 Surgical instrument
110 Main body
120 Shaft
130 Treatment part
150 Movable part
150a Protruding portion
160 Wire
225 Guide groove
225a Wall
500 Medical robot
510 Multi-degree-of-freedom arm
511 Actuator part
512 Control part
520 Mounting portion
550 Power transmission part
550a Protruding portion
560 Stopper
L1, L2, L3 Length
W1, W2 Width

The invention claimed is:

1. A drape unit that is disposed between a medical robot holding a surgical instrument and the surgical instrument to isolate the surgical instrument and the medical robot from each other, the drape unit transmitting power in a forward/backward direction from a power transmission part of the medical robot to a movable part provided in the surgical instrument, the drape unit comprising:
   a movable intervening part that receives the power from the power transmission part; and
   a fixed intervening part that is detachably attached to the medical robot, the fixed intervening part having a through-hole through which a first part of the movable intervening part is inserted,
   the fixed intervening part having a housing portion that covers a second part of the movable intervening part as viewed in a penetrating direction of the through-hole when the movable intervening part moves to an end portion in the forward/backward direction.

2. The drape unit according to claim 1, wherein the movable intervening part has:
   a first movable portion that receives the power from the power transmission part;
   a second movable portion that transmits the power to the movable part; and
   a third movable portion that extends from the second movable portion in the forward/backward direction, and
   the third movable portion has a cover area that is housed in the housing portion.

3. The drape unit according to claim 2, wherein:
   the fixed intervening part is an assembly that comprises a first fixed portion provided with a first opening through which the first movable portion is inserted and a second fixed portion provided with a second opening through which the second movable portion is inserted, and
   the movable intervening part is interposed between the first fixed portion and the second fixed portion and housed in the fixed intervening part so as not to drop off.

4. The drape unit according to claim 3, wherein a length of the second opening in the forward/backward direction is shorter than a length of the first opening in the forward/backward direction.

5. The drape unit according to claim 3, wherein:
   the fixed intervening part has a guide groove that receives the first part of the movable intervening part and guides the movable intervening part to move in the forward/backward direction, and
   in a state in which the drape unit and the surgical instrument are mounted on the medical robot, when viewed in the penetrating direction, predetermined gaps are provided between the third movable portion and the first fixed portion and between the third movable portion and the second fixed portion.

6. The drape unit according to claim 3, wherein the second opening is closed by the third movable portion.

7. The drape unit according to claim 3, wherein a length of the third movable portion in the forward/backward direction is longer than a length of the second opening in the forward/backward direction.

8. The drape unit according to claim 3, wherein in a state before the surgical instrument is mounted on the medical robot, the movable intervening part is disposed so as to close the entire first opening of the fixed intervening part mounted on the surgical instrument.

9. The drape unit according to claim 1, wherein the movable intervening part is configured so as not to come into contact with an inner wall surface that constitutes the through-hole of the fixed intervening part, in a state in which the movable intervening part is located at the end portion in the forward/backward direction.

10. The drape unit according to claim 1, wherein a plurality of the movable intervening parts is arranged in parallel in a direction orthogonal to the forward/backward direction and the penetrating direction.

11. A drape unit comprising:
    a movable part that is configured to transmit power from a medical robot to a surgical instrument; and
    a fixed part that is detachably attached to the medical robot, in which the movable part is inserted,
    wherein the movable part moves in a forward/backward direction in the fixed part between a first end position and a second end position opposite to the first end position, and
    the fixed part houses the movable part when the movable part moves to the first end position and to the second end position in the forward/backward direction.

12. The drape unit according to claim 11, wherein the movable part receives a power transmission part of the medical robot and a protruding portion of the surgical instrument.

13. The drape unit according to claim 11 wherein,
    the fixed part comprises an elongated through hole into which the movable part is inserted.

14. The drape unit according to claim 11,
    wherein the movable part comprises:
    a first portion that is configured to receive a power transmission part of the medical robot;
    a second portion that is configured to receive a protruding portion of the surgical instrument; and
    a third portion that extends from the first portion and the second portion in the forward/backward direction.

15. The drape unit according to claim 14,
    wherein the fixed part comprises:

a first fixed portion with first elongated holes extending in the forward/backward direction and through which the first portion is inserted, and a second fixed portion with elongated holes extending in the forward/backward direction and through which the second portion is inserted, and wherein the first elongated holes and the second elongated holes guide the movable part to move in the forward/backward direction between the first end position and the second end position.

16. The drape unit according to claim 15, wherein when the movable part is located at the first end position and the second end position, the first fixed portion of the fixed part covers the third portion of the movable part.

17. A drape unit comprising:
a first fixed portion comprising a plurality of first elongated holes;
a second fixed portion comprising a plurality of second elongated holes; and
a plurality of movable parts, each movable part comprising a first portion extending into a respective one of the plurality of first elongated holes and a second portion extending into a respective one of the plurality of second elongated holes, the plurality of movable parts being independently moveable in a forward/backward direction along the respectively ones of the plurality of first elongated holes and the plurality of second elongated holes,
wherein the second fixed portion has a housing that houses the plurality of movable parts when the plurality of movable parts are at respective ends of the plurality of first elongated holes and the plurality of second elongated holes in the forward/backward direction;
wherein the first portion of each movable part comprises a first recesses for receiving a respective power transmission part of a medical robot, and the second portion of each movable part comprises a second recess for receiving a respective protruding portion of a surgical instrument.

18. A drape unit according to claim 17, wherein a width of each of the plurality of first elongated holes is the same as a width of each of the plurality of second elongated holes, and
each of the plurality of first elongated holes has a first length and each of the plurality of second elongated holes has a second length, and the second length is shorter than the first length.

19. A drape unit according to claim 18, wherein:
edges of a second elongated hole of the plurality of second elongated holes in the forward/backward direction are located inside edges of a corresponding one of first elongated holes in the forward/backward direction.

20. A drape unit according to claim 18 wherein:
each movable part comprises a third portion between the first portion and the second portion, the third portion extending in the forward/backward direction, and
each of the plurality of second elongated holes is entirely closed by the third portion of a respective one of the plurality of movable parts regardless of a position of the respective one of the plurality of movable parts in the second elongated hole.

\* \* \* \* \*